United States Patent [19]
Leavitt

[11] B 3,989,592

[45] Nov. 2, 1976

[54] WATER-SOLUBLE POLYMERS AND UTILIZATION THEREOF

[75] Inventor: Richard Irwin Leavitt, Lower Makefield Township, Pa.

[73] Assignee: Mobil Oil Corporation, New York, N.Y.

[22] Filed: Nov. 23, 1973

[21] Appl. No.: 418,489

[44] Published under the second Trial Voluntary Protest Program on January 13, 1976 as document No. B 418,489.

[52] U.S. Cl. .............................. 195/29; 260/112 R
[51] Int. Cl.$^2$ ........................................ C12D 13/06
[58] Field of Search .................... 195/29; 260/112 R

[56] References Cited
UNITED STATES PATENTS
3,761,353   9/1973   Noe ...................................... 195/29

*Primary Examiner*—Alvin E. Tanenholtz
*Attorney, Agent, or Firm*—Charles A. Huggett; Vincent J. Frilette

[57] ABSTRACT

Water-soluble polymers that thicken reversibly in aqueous solution on alteration of the degree of alkalinity are manufactured by treating an aqueous suspension of protein with the enzymes elaborated extracellularly by a species of the genus Pseudomonas. The water soluble polymers resulting therefrom are biodegradable. They are useful for stabilizing emulsions, as flow-control agents in water base paint, and as anti-redeposition agents in laundry detergents. They are particularly useful as coagulants for colloidal suspensions of solids such as the phosphate slimes byproduct of the large scale hydraulic mining of phosphate deposits. They are also particularly useful as flow control agents in the water flooding process for the recovery of petroleum.

11 Claims, No Drawings

WATER-SOLUBLE POLYMERS AND UTILIZATION THEREOF

FIELD OF THE INVENTION

This invention is concerned with the enzymatic modification of high molecular weight polymers. It is particularly concerned with the enzymatic modification of water-dispersible proteins. This invention is further concerned with a method for preparing novel, modified water-soluble polymers that exhibit marked thickening effects in dilute solution. This invention is further concerned with a method for coagulating colloidal suspensions of microfine particles, such as phosphate slimes, by addition thereto of a small proportion of a modified protein polymer. This invention is further concerned with an improved method for water-flooding oil wells.

DESCRIPTION OF PRIOR ART

A limited number of useful high molecular weight synthetic polymers that are soluble in water are known. Among these are partially hydrolyzed polyacrylamide, methyl cellulose, a polysaccharide known as KELZAN, and various polyalkylene oxides. Members of this group have utility in such diverse fields as food preparations, laundry detergents and cosmetic preparations. In general, the members of this class of materials are expensive because the synthetic procedures required for their preparation are involved and costly. Furthermore, specific members of this class which at low concentrations impart very high viscosity to water solutions are particularly difficult to dissolve and manipulate.

One application for members of this class of water-soluble polymers is concerned with slime waste produced by the phosphate mining industry. Typical slimes from a beneficiation plan have a solids concentration of from about 0.5 to 5%. The solids in suspension consist largely of hydrophilic clays such as attapulgite and montmorillonite, in addition to very fine particles of unrecoverable phosphate mineral. The slimes are produced in enormous quantities and have been accumulated almost since the inception of the phosphate industry, some fifty years ago. The industry has stored these slimes behind dikes over large areas of land where they eventually dewater to a solid concentration usually less than about 30%. Thus, the industry and the public are burdened with constantly growing areas of blighted land which have not been recoverable. A process for the treatment of phosphate slimes is described in U.S. Pat. No. 3,680,698. In this process, a small amount of water soluble polymeric coagulant is formed in situ in the slime suspension, and the flocculated solids that result can be dewatered effectively on admixture with a filtering aid such as sand.

Another potential application for members of this class of polymers is in the recovery of petroleum. It is well known that only about 50% of the oil contained in a porous formation is recoverable by the usual (primary) methods. Injection of huge quantities of water into the petroleum reservoir results in recovery of another small fraction of the oil from the production well. This technique is commonly referred to as waterflooding, or secondary recovery.

The industry now seeks more advanced technology since as much as 33% of the original oil still defies displacement from the formation by simple water-flooding.

So-called "tertiary recovery methods" have been proposed which are designed to improve the effectiveness of water-flooding. One version of tertiary recovery requires addition of a surfactant and also a polymer to a portion of the water that is to be injected into the porous formation. The surfactant is believed to cause the water to more efficiently displace the oil in the formation. The "water thickening" polymer controls the flow in such a manner that the injected water moves with an even front through the formation, pushing the oil ahead of it. It is believed that this combination of surfactant and flow control agent, under favorable circumstances, can recover substantial quantities of oil, perhaps even all of the oil in the formation. This is certainly a desirable technology to develop, since it would increase the recoverable reserves of petroleum, which is a non-replenishable resource. However, the development and largescale use of this technology depends on the availability of lowcost, highly efficient and easily processed water-soluble polymer because the quantities required are huge.

Two types of water soluble polymers have been identified as potentially useful flow control agents. one of these is a high molecular weight hydrolyzed polyacrylamide. While this material effectively thickens water at low concentrations, it rapidly loses its thickening effect when the injected slug begins to mix with the brines normally present in the porous formation. It suffers from the further defect of being degraded in molecular weight and effectiveness under the shearing stress to which it is subjected in the pumping operation. It is also a very expensive polymer. A second type which has been identified as useful for this purpose is a polysaccharide known as KELZAN, which is prepared as described in U.S. Pat. No. 3,427,226. KELZAN is a biopolymer produced by the fermentation of glucose, utilizing a special variety of microorganism. Because the microorganism must build this polymer from small molecules, the fermentation time is long; and, because the polymer is an effective thickening agent in the fermentation broth, the fermentation stops when only 2% by weight of the polymer is contained in the broth. Thus, the production of the polymer is very costly.

It is an object of this invention to provide a novel simple method for synthesizing novel water-soluble polymers. It is a further object of this invention to convert inexpensive, readily available proteinaceous materials to novel water-soluble polymers. It is a further object of this invention to provide novel biodegradable polymers that form non-Newtonian aqueous solutions. It is a further object of this invention to provide novel polymers that thicken water at low concentrations. It is a further object of this invention to provide an improved method for dewatering phosphate bearing slimes. It is a further object of this invention to provide an improved method for the tertiary recovery of petroleum. It is a further object of this invention to provide a novel nontoxic, water-soluble colloid useful in paint, cosmetic, and laundry detergent formulations. Other objects will become evident to those skilled in the art.

BROAD DESCRIPTION OF THE INVENTION

It has now been discovered that readily available, inexpensive proteins may be converted to unusual water-soluble polymers by contact with the enzymes proliferated extracellularly by a particular microorganism. The proteins which are referred to are the waterdispersible proteins that may be derived from a variety of vegetable or animal sources.

It has now been found, surprisingly, that water suspensions of dispersible proteins, when innoculated and incubated with a particular organism as hereinbelow described, are altered in a relatively short time to form the novel water-soluble polymers of this invention. Their presence is evidenced for example, by marked increase in the viscosity of the suspension on increasing its pH to above about 9. The protein suspension, prior to innoculation, is relatively unaffected by the addition of alkali. In some instances, alkalizing the suspension after incubation according to this invention not only increases its viscosity but causes it to exhibit marked memory effects. Such an alkalized suspension, partially poured from one beaker into a lower beaker, will flow against gravity back into the first beaker if it is restored to a non-tilted position. On reduction of the alkalinity, the viscous solution reverts to its former state, i.e. the marked thickening induced by alkalinity is reversible.

The water-soluble polymers of this invention were found to be very effective flocculating agents for phosphate slimes. Very dilute solutions of the polymers, as will hereinafter be described, were found also to have the property of very effectively displacing crude oil held in the pores of compacted sand. These polymers have other useful properties, as will be shown.

DETAILED DESCRIPTION OF THE INVENTION

The proteins that may be treated by the method of this invention include a wide variety of substances derived from vegetable or animal sources. While it is difficult to classify proteins in any simple, completely satisfactory manner, is is believed that the best results in the practice of this invention are achieved with water-dispersible proteins, and in particular with those types of water-dispersible proteins classified as globulins, which are precipitated from aqueous solution by 50% saturation with ammonium sulfate, and as albumins, which are soluble in pure water, coagulated by heat, and precipitate from solution only at ammonium sulfate concentrations in excess of 50% of saturation. Water insoluble proteins such as keratins, which are the structural proteins of such things as hair, wool, and feathers are not suitable.

Natural proteins, i.e. those formed in living cells and tissues, are preferred for use in this invention. Some of these are readily available at low cost. However, It is conceivable to treat synthetic proteins by the method of this invention.

Relatively pure, simple proteins such as Ovalbumin derived from the egg white of hen's eggs may be used in this invention. This protein has a molecular weight of about 45,000, and its molecules contain a small amount of carbohydrate and phosphoric acid ester groups in addition to amino acids. It has a nitrogen content of 15.6%. The protein is water-soluble. Less pure albumins, such as whole egg white and blood serum, may be used.

Most proteins occur in nature as complex mixtures. Many of these proteins are classified as globulins, and may require the presence of some sodium chloride or other salt to form a true solution in water. In some cases, one or more of the proteins in a mixture may be tenuously attached to the cellulosic components with which it occurs in nature. In some instances the protein molecule is complex and contains a significant complement of sugar molecules or phospholipid structures. In any case, these natural protein mixtures, as more specifically described herein below, often interact with water with some portion going into true or colloidal solution and some portion merely swelling. Such mixtures will be referred to in this specification as water-dispersible proteins. As used in this invention, the term water-dispersible protein will be understood to include proteins and mixtures of proteins that form true or colloidal solutions in pure water, those proteins which require addition of a salt to form a true or colloidal solution, and also mixtures thereof.

It is a feature of this invention that the novel water-soluble polymers are efficiently formed not only from pure simple proteins such as Ovalbumin but also from crude mixtures of proteins which are water-dispersible. Furthermore, the crude mixtures may contain non-protein constituents such as cellulosic residues, other carbohydrates, fats and resinous substances. For the efficient practice of this invention, however, the proteinaceous solid should contain at least 20 % protein calculated on a water-free basis, as evidenced by a nitrogen content of at least 3.2%N, and preferably at least 40% protein as evidenced by a nitrogen content of at least 6.4%N. It is to be understood that nitrogen content refers to the weight percent organic nitrogen of the dried solids as usually determined by the well-known Kjehldahl technique.

Many of the proteins suitable for use in the present invention occur within individual cells of an organism where they are contained by a cell wall or cell membrane. Under these circumstances, it is essential for the purpose of this invention that these walls be ruptured so that the protein molecule becomes available for enzymatic modification. This may be achieved by any one of a number of techniques known to those skilled in the art of microbiology. For example, the tissues and cell walls may be ruptured by a mechanical treatment such as grinding, or by temperature cycling to induce freezing and thawing, or by ultrasonic vibration, or by chemical or other means. In general, it is desirable to induce rupture of the cell walls under conditions that are not likely to denature the protein, which could make the protein less reactive.

Various fat-bearing seeds are excellent sources of protein since they are inexpensively available as by-product from oil manufacture. Seeds which may be used in this manner are; cottonseed, linseed, soy bean, peanut, castor bean, sesame seed, corn, and other such materials. It is common practice to recover oils from these materials by subjecting them to pressure to expel the fatty oils. This operation results in rupture of the cell membranes, and leaves a solid residue, commonly referred to as a "meal." This meal can be further defatted by contact with suitable solvents, although this step is not necessary for the practice of this invention. The protein from the meal can be further recovered and refined, although it is a feature of this invention that this step is not necessary. Defatted cottonseed meal is a preferred water-dispersible protein.

In addition to fat-bearing seeds as a source of protein, other sources may be used such as beef extract, blood serum, fish meal protein, and single-cell protein. The previously specified protein content of the proteinaceous solids applies to these sources, too, but it should be understood that the solids of dissolved proteins, e.g. blood serum, need not be separated prior to use in this invention.

The present invention is based on the discovery that a particular strain of microorganism, when grown in the presence of the described protein, transforms the protein to a novel watersoluble polymer that exhibits unusual properties in aqueous solutions. This microorganism *Pseudomonas fabricans* No. 492(A.T.C.C. No.21984), has the following characteristics: it may be grown on a thiophene substrate as the sole carbon source; it is capable of growing on hydrocarbons as the carbon source; it is a gramnegative organism with a rod-like cell; and it is believed to be a variety in the *Pseudomonas genus*. The microorganism can be lyophilized without destruction. A sample of this microorganism *Pseudomonas fabricans* No. 492 (A.T.C.C. No. 21984) has been deposited with the American Type Culture Collection, located at 12301 Parklawn Drive, Rockville, Maryland, 20852, under an irrevocable agreement to make the organism available to the public on issuance of this patent.

In the practice of this invention, any of the proteinaceous materials described may be suspended in water at a concentration from 0.1 to 15.0%, the mixture adjusted to a pH of from about 6.0 to about 8.0 with a buffer, and the suspension innoculated with the Pseudomonas organism (A.T.C.C. No.21984). Other inorganic elements necessary to the fermentation are introduced as salts in a manner and in amounts well known to those skilled in the art. Subsequently the suspension of protein is incubated aerobically for a period of from about 2 hours to about 72 hours, at a temperature from about 20°C to about 40°C. The resultant mixture contains the novel water-soluble polymer product of this invention.

As a variant of the above procedure, the microorganism may be grown in the absence of the protein raw materials, the extracellular enzymes recovered, and the enzymes added to the protein suspension to convert it to the novel water-soluble polymer.

As a further variant on the above procedures, it is possible to incorporate hydrocarbon, carbohydrate or other nonproteinaceous carbon-containing nutrients in the innoculated protein suspension. The hydrocarbon, e.g., is added at a concentration from 0.1 to 10% of the volume of water used. The provision of such a substrate as a hydrocarbon is advantageous since it minimizes the consumption of protein by the organism for growth purposes, and maximized the yield of water-soluble polymer.

It is a feature of this invention that the novel water-soluble polymers may be produced by the techniques described without resorting to sterile procedures, if desired.

The water-soluble polymer in solution and resulting from the incubation may be used without further refinement, or alternatively it can be refined to a greater or lesser degree depending on end use. For example, solid residues including the microorganisms may be separated from the modified protein polymer solution by centrifugation, or these solids may be separated by filtration, preferably while the solution is at a pH of about 7 to facilitate separation. The solid polymer may be obtained by spray-drying the filtered or centrifuged solution if it is desired to remove the water. Or, the incubated product may be dried without filtration or centrifugation. For some applications, extensive refinement of the water soluble polymers may be desired. This may be done by removing particulate matter, as described, and precipitating the polymer by the addition of a solvent such as alcohol or acetone. The solids so recovered will be free of salts, carbohydrates and other extraneous matter.

The water-soluble polymer solutions have the property of markedly increasing viscosity as the pH is raised from the fermentation range pH of 6 to 8 to a pH value greater than about 9.0. This property is very advantageous, since relatively concentrated solutions of the polymer may be prepared at low viscosity at a pH of about 7.0, stored, pumped, or mixed readily with solids or with more water, and the viscosity may thereafter be increased dramatically by the addition of alkali to increase the pH. The viscosity dependence on pH is a reversible phenomenon, that is, the thickened polymer may be thinned by decreasing the pH. Sodium chloride, a salt, may be present in the polymer solution without materially affecting the thickening phenomenon.

The transformation of various proteins from such diverse sources as cottonseed meal and beef extract to the water-soluble polymers of this invention is not fully understood. However, it may be postulated that an enzymatically induced molecular modification is responsible for the transformation, and that this modification allows the molecules to acquire an extended configuration in alkaline solutions, probably accompanied by an association of individual molecules to form very high molecular weight aggregates. This hypothesis is suggested by the pseudoplastic properties of alkaline solutions of the water-soluble polymers, i.e. their reversible reduction in viscosity as the rate of shear is increased, the unusually high viscosity of very dilute solutions and evidence of incipient elastic gel structure in more concentrated solutions. It is believed, however that the water-soluble polymers of this invention retain a large fraction of the amide linkages characteristic of the proteins, i.e. that they contain organically bound nitrogen and have a nitrogen content greater than 10 weight percent.

The novel water-soluble polymers of this invention are effective coagulants for a variety of suspensions, including phosphate slimes. For this application, water-soluble polymer is added in amounts up to about 1.0% by weight of the slime, and preferably in amounts not exceeding 0.2% by weight, and the pH adjusted to from 9.5 to 12.0 to induce flocculation. The watersoluble polymer need not be isolated from the broth produced by incubation of the innoculated aqueous suspension of protein.

Solutions of the novel water soluble polymers of this invention may be used in the tertiary recovery of petroleum from spent oil wells. For this method, a solution of the polymer of up to about 2% concentration, and at a pH of about 11, is introduced by injection into oil-bearing rock formation. Surfactant such as petroleum sulfonate may be mixed with the novel water soluble polymer in concentrations of up to 0.5%. As a variant, the water-soluble polymer may be injected into the borehole at a pH of about 7 and concentrated alkali solution independently introduced via a separate feed line to induce thickening of the polymer solution below ground.

other applications for the water-soluble polymers of this invention include stabilizing the suspension of solids such as pigments, for which concentrations of from about 2% to about 10% of the total composition are used. Such concentrations are also useful for stabilizing emulsions of hydrocarbon fluids and fatty oils in water for the preparation of lubricant fluids, for example.

Other applications will be evident to those skilled in the art.

The method for the preparation of the water-soluble polymers of this invention and the utilization thereof is further illustrated by the following examples, but this invention is not limited thereto.

EXAMPLE 1

A sulfur-free mineral salts medium of the following composition (grams per liter) was prepared:

$Na_2HPO_4$, 3.0
$KH_2PO_4$, 2.0
$MgCl_2 \cdot 6H_2O$, 0.2
$FeCl_3 \cdot 6H_2O$, 0.028
$NH_4Cl$, 2.0
Beef Extract, 5.0.

The medium was solidified by the addition of 2% agar. A Petri dish containing 20 ml of the solidified media was streaked with a 0.1 ml suspension of the organism *Pseudomonas fabricans* No.492 (A.T.C.C. No. 21984). Dibenzothiophene was added as a powder to the surface of the agar plate. After 48 hours incubation at 25°C, the culture was suspended in 5 milliliters of water and the suspension was used as innoculum.

This example illustrates the preparation of an active innoculant.

EXAMPLE 2

The following composition was prepared:

| | | |
|---|---|---|
| $Na_2HPO_4$ | 3.0 | grams per liter |
| $KH_2PO_4$ | 2.0 | " |
| Petroleum residuum derived from the atmpshereic pressure distillation of a West Texas crude oil | 8.5 | " |
| Cottonseed meal | 10.0 | " |

The cottonseed meal of this example was a meal prepared by a lowtemperature oil extraction process to avoid extensive denaturation of the globulius. It was purchased under the trade name PHARMAMEDIA from the Trader's Protein Division of Traders Oil Mill Co., Ft. worth, Texas, and had a total solids content of 95%, and analyzed 56% protein. Twenty milliliters of this composition having a pH of 7.0, contained in a 250 milliliter Ehrlenmeyer flask, was innoculated with 0.5 ml innoculum of Example 1. It was aerobically incubated at 34°C with shaking for 17 hours. At this point the viscosity of the suspension was about 1.5 centipoise. The composition visibly thickened on gradual addition of dilute NaOH solution. Thickening was apparent at a pH of about 10.0, and increased to a pH of about 11.5.

EXAMPLE 3

To 100 ml of the thickened solution of example 2 was added 800 milliliters of isopropyl alcohol, which resulted in the precipitation of about 0.28 grams of a hard, brownish-colored product. The product was isolated and excess isopropanol removed. Of the product, 0.25 grams was added to 100 ml of water. Although some disaggregation occurred, there was negligible thickening of the water. The pH was raised to 11.5 and the temperature was brought to 50°C, resulting in the formation of a dark brown dispersion characterized by a stable viscosity of 6 centipoise.

EXAMPLE 4

One liter of protein suspension was prepared as in Example 2 except that 100 grams of the cottonseed meal was used intead of 10 grams. The suspension was innoculated and incubated for seventeen hours, as in Example 2. The final product was a thin fluid and had a pH of about 8.2. The suspension became extremely viscous on addition of alkali.

EXAMPLE 5

One liter of distilled water containing 3.0 grams of $Na_2HPO_4$ and 2.0 grams of $KH_2PO_4$ was prepared in a 2-liter shake flask. One hundred grams of the cottonseed meal described in Example 2 was added to the solution together with 5cc of the innoculum described in Example 1. The mixture was incubated aerobically at 34°C for 48 hours.

The incubated mixture was centrifuged at 600xg for 15 minutes, followed by filtration through a coarse sintered glass filter to remove suspended solids. The filtrate was a thin fluid.

A portion of the filtrate was adjusted to pH 11.2 with sodium hydroxide. Its viscosity at two shear rates, at room temperature, was measured with a Brookfield rotational viscometer, with the following results:

| Spindle Speed | Viscosity |
|---|---|
| 60 R.P.M. | 500 centipoise |
| 12 R.P.M. | 625 centipoise |

This solution, diluted with four parts of distilled water, had the following viscosities:

| Spindle Speed | Viscosity |
|---|---|
| 60 R.P.M. | 155 centipoise |
| 30 R.P.M. | 250 centipoise |

EXAMPLE 6

To 100 milliliters of phosphate buffer containing 3.0 grams per liter of $Na_2HPO_4$ and 2.0 grams per liter of $KH_2PO_4$ was added 10 grams of purified egg albumin. The solution was innoculated with 0.5 milliliters of the innoculum described in Example 1, at which point it had a pH of 7.0. It was then incubated for 17 hours at 34°C, after which it exhibited a pH of 8.4. The pH was adjusted to 11.4 causing the liquid to become extremely viscous.

EXAMPLE 7

2.0 milliliters of 10% blood serum was added to 20 milliliters of distilled water. The solution was innoculated with the innoculum of Example 1 and incubated with shaking for 17 hours. Addition of base after incubation caused the product to become moderately viscous.

EXAMPLE 8

A solution with the following composition was prepared:

| | | |
|---|---|---|
| $Na_2HPO_4$ | 3.0 | grams per liter |
| $KH_2PO_4$ | 2.0 | " |
| $MgCl_2 \cdot 6H_2O$ | 0.2 | " |
| $FeCl_3 \cdot 6H_2O$ | 0.028 | " |

-continued

| | | |
|---|---|---|
| NH₄Cl | 2.0 | " |
| Dibenzothiophene | 2.5 | " |

Four twenty-milliliter portions of this solution were taken and to these were added none, 0.25%, 0.50% and 1.0%, respectively of beef extract. The beef extract was an article of commerce purchased from Difco laboratories, Detroit, Michigan. All four aliquots were innoculated with the innoculum described in Example 1, and were then shaken for 72 hours. The incubated aliquots thickened on addition of alkali to a degree depending on the initial protein content, as follows:

| % Beef Extract | Observed Thickening |
|---|---|
| 0 | none |
| 0.25 | slight |
| 0.50 | marked |
| 1.0 | very marked |

EXAMPLE 9

A field sample of slimes waste from a Florida phosphate mining operation was found to contain 7.5 weight percent suspended solids. 0.5 milliliter of the thickened product described in Example 1 was added to 10 milliliters of the slime and the whole shaken. To another 10 milliliter aliquot of slime was added 0.2 milliliter of 0.1 Normal HCl solution and 0.5 milliliter of the thickened product described in Example 2, followed by shaking. Another 10 milliliter aliquot of untreated slime was shaken. After one hour standing the untreated aliquot showed no flocculation as evidenced by settling. The aliquot treated with the polymer solution showed 50% sedimentation with a cloudy supernatant layer and the aliquot treated with polymer solution and acid showed 55% sedimentation with a clear supernatant layer.

EXAMPLE 10

A suspension of 2 weight percent attapulgite clay in distilled water was prepared. The suspension did not sediment after 72 hours. Addition of one milliliter of the thickened polymer described in example 2 to 10 milliliters of the clay suspension resulted in a flocculated, settled layer of about 2.5 milliliters volume and a supernatant volume of 7.5 milliliters in 72 hours. A parallel experiment substituting a 1% solution of KELZAN for the polymer solution was ineffective.

EXAMPLE 11

A 2½-inch diameter glass tube was drawn down to one eighth of an inch at one end and mounted vertically in a holder. Into the tube was placed a layer of glass beads followed by a layer of coarse gravel. Ten cubic centimeters of crude oil is poured into the tube followed by sufficient clean sand to absorb the oil. This assembly simulates oil-bearing rock.

Air was blown through the bed to drain excess oil followed by a water rinse which displaced most of the unadsorbed oil. Five tenths of a milliliter of the thickened solution of Example 2 was diluted to 5 milliliters and poured onto the oilwet sand and allowed to drain through the bed. This was followed by an excess of 1% sodium chloride solution. The polymer solution visibly displaced oil, which was recovered from the collected polymer solution and brine.

EXAMPLE 12 a water-dilutable cutting oil concentrate was prepared by mixing together in a Waring blender:

| | |
|---|---|
| Furfural refined hydrocarbon oil,200 S.U.S. at 100°F | 10 c.c. |
| Filtered water dispersible polymer solution of Example 5, adjusted to pH of 11.2 | 20 c.c. |

The mixture formed a tan-colored emulsion having an estimated viscosity of about 100 cps.

What I claim is:

1. A process for manufacturing watersoluble polymers that thicken reversibly in aqueous solution on adjustment of the degree of alkalinity, which comprises contacting, under conversion conditions, an aqueous suspension of a water-dispersible protein with the extracellular enzymes formed by the microorganism *Pseudomonas fabricans* No. 492 (A.T.C.C.No.21984), said enzymes being in an amount effective to produce said reversible thickening.

2. A process for manufacturing water-soluble polymers that thicken reversibly in aqueous solution on adjustment of the degree of alkalinity, which comprises: preparing an aqueous suspension of a water-dispersible protein; innoculating said suspension with the microorganism *Pseudomonas fabricans* No. 492(A.T.C.C. No.21984), and incubating the innoculated suspension for about 2 to 35 hours whereby said water soluble polymers are formed.

3. The process described in claim 2 in which the waterdispersible protein comprises globulins.

4. The process described in claim 2 in which the waterdispersible protein comprises albumins.

5. The process described in claim 2 in which the waterdispersible protein is the meal produced by pressing a fat-bearing seed to recover an oil.

6. The process described in claim 5 in which the waterdispersible protein is cottonseed meal.

7. The process described in claim 5 in which the waterdispersible protein is soybean meal.

8. The process described in claim 2, including the additional step of adding from 1 to 10 wt. percent of a hydrocarbon liquid to said aqueous suspension prior to incubation.

9. The process described in claim 2, and including the step of separating suspended solids from said incubated suspension whereby to produce a substantially clear water solution of water-soluble polymers.

10. A process for the manufacture of water-soluble polymers that thicken reversibly in aqueous solution on adjustment of the degree of alkalinity, which comprises: preparing a first aqueous suspension of a water-dispersible proteinaceous solid; preparing a second aqueous suspension of the microorganism *Pseudomonas fabricans* No. 492 (A.T.C.C.No.21984) including nutrients and growth factors; incubating said second suspension for a time sufficient to induce the formation of quantities of extracellular enzymes effective to produce said reversible thickening; mixing a major quantity of said first suspension with a minor quantity of said incubated second suspension; and holding said admixture under conversion conditions for a time sufficient to enzymatically form said water-soluble polymers.

11. The process described in claim 10 and wherein, additionally; the said first and second aqueous suspensions are respectively adjusted to a pH of about 7.

* * * * *